(12) United States Patent
Jones et al.

(10) Patent No.: US 6,699,222 B1
(45) Date of Patent: Mar. 2, 2004

(54) CONTOURED SYRINGE AND NOVEL LUER HUB AND METHODS FOR EMBOLIZING BLOOD VESSELS

(75) Inventors: Michael L. Jones, Capistrano Beach, CA (US); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/197,525

(22) Filed: Nov. 23, 1998

Related U.S. Application Data

(62) Division of application No. 08/866,208, filed on Jun. 13, 1997.

(51) Int. Cl.[7] ................................................ A61M 5/00
(52) U.S. Cl. ..................... 604/187; 604/181; 604/93.01
(58) Field of Search ............................... 604/174, 180, 604/187, 181, 93.01

(56) References Cited

U.S. PATENT DOCUMENTS

| | | | |
|---|---|---|---|
| 2,755,801 A | | 7/1956 | Morando |
| 2,767,710 A | * | 10/1956 | Blackman ................... 128/218 |
| 3,055,363 A | * | 9/1962 | Eckhart ....................... 128/218 |
| 3,491,757 A | | 1/1970 | Arce |
| 3,977,403 A | | 8/1976 | Patel |
| 4,232,670 A | | 11/1980 | Richter et al. |
| 4,477,255 A | | 10/1984 | Pasztor et al. |
| 4,739,768 A | | 4/1988 | Engelson |
| 4,842,590 A | | 6/1989 | Tanabe et al. |
| 4,874,377 A | * | 10/1989 | Newgard et al. ........... 604/167 |
| 4,886,506 A | | 12/1989 | Lovgren et al. |
| 5,064,416 A | * | 11/1991 | Newgard et al. ........... 604/167 |
| 5,084,023 A | * | 1/1992 | Lemieux ..................... 604/167 |
| 5,234,410 A | * | 8/1993 | Graham et al. ............. 604/167 |
| 5,346,480 A | * | 9/1994 | Hess et al. ................... 604/197 |
| 5,470,318 A | * | 11/1995 | Griffith, III et al. ........ 604/161 |
| 5,695,480 A | * | 12/1997 | Evans et al. ................. 604/264 |
| 5,782,803 A | * | 7/1998 | Jentzen ........................ 604/110 |
| 5,785,679 A | | 7/1998 | Abolfathi et al. |
| 5,792,099 A | | 8/1998 | DeCamp et al. |
| 5,795,340 A | | 8/1998 | Lang |
| 5,902,270 A | * | 5/1999 | Jentzen ........................ 604/110 |
| 5,989,219 A | * | 11/1999 | Villas et al. ................. 604/110 |

FOREIGN PATENT DOCUMENTS

| | | |
|---|---|---|
| DE | 4306136 | 8/1994 |
| WO | WO 91/07203 | 5/1991 |

OTHER PUBLICATIONS

Chaloupka, John C., et al., "Technical Feasibility and Histopathologic Studies of Ethylene Vinyl Copolymer (EVAL) Using a Swine Endovascular Embolization Model," AJNR 15: 1107–1115, Jun. 1994.

Laurent, A., et al., "Injectable Gel–Giving Solutions for Embolization: Hydrodynamic and Animal Studies," Abstract No. 299, Meeting of Interventional Radiology, 1996.

Sampei, K., et al., "Histological Changes in Brain Tissue and Vasculature After Intracarotid Infusion of Organic Solvents in Rats," Interventional Neuroradiology 38: 291–294, 1996.

* cited by examiner

*Primary Examiner*—Henry Bennett
*Assistant Examiner*—Nihir Patel
(74) *Attorney, Agent, or Firm*—Swiss Law Group LLC

(57) ABSTRACT

Disclosed are novel syringes and catheters for delivering compositions which form solid masses in vivo. These syringes and catheters are particularly useful for delivering embolizing compositions intravascularly.

7 Claims, 3 Drawing Sheets

CONTOURED SYRINGE AND NOVEL LUER HUB AND METHODS FOR EMBOLIZING BLOOD VESSELS

This application is a divisional, of application Ser. No. 08/866,208, filed Jun. 13, 1997.

BACKGROUND OF THE INVENTION

1. Field of the Invention

This invention relates to novel syringes and catheters for delivering compositions which form solid masses in vivo. These syringes and catheters are particularly useful for delivering embolizing compositions in situ (e.g., intravascularly).

2. State of the Art

The delivery of fluid compositions which solidify in vivo is particularly useful for a variety of reasons including embolization of blood vessels in the treatment of tumors, aneurysms, arteriovenous malformations ("AVMs"), arteriovenous fistula ("AVF"), uncontrolled bleeding and the like, as well as in the sterilization of mammals by blocking the vas deferens or fallopian tubes, in the treatment of urinary incontinence by the addition of a bulking agent to the periurethral tissue and the like.

Delivery of such compositions is preferably accomplished via catheter techniques which permit the selective placement of the catheter at the delivery site. For example, recent advancements in catheter technology as well as in angiography now permit neuro endovascular intervention including the treatment of otherwise inoperable lesions. Specifically, development of microcatheters and guide wires capable of providing access to vessels as small as 1 millimeter in diameter allows for the endovascular treatment of many lesions.

Catheter delivery for in vivo solid mass formation can employ fluid compositions which comprise a solvent such as ethanol, dimethylsulfoxide ("DMSO"), or aqueous solutions of ethanol or DMSO, a biocompatible water insoluble polymer, and a water insoluble contrast agent. Preferably, however, the solvent is non-aqueous in order to maximize the amount of biocompatible water insoluble polymer which can be dissolved therein.

In practice, the catheter tip is directed to the vascular or other delivery site by use of an aqueous solution containing an aqueous based contrast agent which permits the physician to visualize the catheter tip under conventional techniques such as fluoroscopy, and the like. After placement of the catheter, the composition is introduced into the catheter and delivered to this site. Upon delivery, the solvent dissipates into the blood, fluid or tissue and the water insoluble polymer and contrast agent precipitate to form a coherent mass which solidifies in vivo.

In embolic procedures, for example, the solvent is selected to be miscible or soluble in blood or other body fluid and to solubilize the water insoluble biocompatible polymer during delivery. The biocompatible polymer is selected to be soluble in the solvent but insoluble in blood or other body fluid. The contrast agent is suspended in the composition to provide for a deliverable fluid and, as above, is selected to permit the physician to fluoroscopically or otherwise visualize catheter delivery of this composition. Upon contact with the blood or other body fluid, the solvent dissipates from the composition whereupon the biocompatible polymer precipitates in the presence of the water insoluble contrast agent and, in the case of delivery to blood vessels, embolizes the blood vessel.

A problem may arise, however, when this composition is injected at the delivery site after delivery of an aqueous solution such as an aqueous solution containing a contrast agent. Specifically, it has been found that the catheter line can become plugged due to premature precipitation of the biocompatible polymer which plugging, of course, interferes with delivery of the composition to the specific site in vivo.

SUMMARY OF THE INVENTION

This invention, generally speaking, provides syringes and catheters which inhibit premature precipitation of fluid compositions which form solid masses in vivo.

This invention provides novel syringes particularly useful for avoiding premature precipitation of a fluid composition designed to form a solid mass in vivo. This invention also provides novel catheters for delivering such compositions to in vivo sites. In a preferred embodiment, the syringe is used in combination with the novel catheter for use in methods of in vivo embolization of blood vessels.

In one aspect, this invention addresses the problem of premature precipitation of a biocompatible polymer in a fluid composition designed to form a solid mass in vivo by providing for a novel syringe which syringe comprises:

(a) a body for holding a fluid composition;

(b) an ejection port having an annular wall and an orifice therethrough which extends from the syringe body to a distal end of said port wherein said annular wall is tapered at the distal end along the length of at least a portion of the ejection port;

(c) a means for ejecting the fluid composition out of the syringe, and (d) a means for mating the syringe body to a catheter luer hub.

In a preferred aspect of the invention, the syringe is mated with a microcatheter luer hub.

In another aspect, this invention addresses the problem of premature precipitation of a biocompatible polymer in a fluid composition by providing for a catheter comprising (a) a luer hub body for holding a fluid composition and a delivery means attached to luer hub body wherein the luer hub body has a maximal volumetric capacity of no more than 0.2 cc, and (b) at least one means for mating the luer hub body to a syringe.

In one of its method aspects, this invention provides a method for inhibiting premature precipitation of a biocompatible polymer of a fluid composition designed to form a solid mass in vivo which composition is delivered by a microcatheter to a vascular site of a mammal where it precipitates and embolizes the vascular site. In this method, the composition is selected and placed into a syringe. The syringe comprises:

(a) a syringe body for holding a fluid composition, (b) an ejection port having an annular wall and an orifice which extends from the syringe body to a distal end of said port wherein said annular wall is tapered at the distal end along the length of at least a portion of the ejection port, (c) a means for ejecting the fluid composition in the syringe body through the ejection port and out of the syringe; and (d) a means for mating said syringe body to a catheter luer hub.

A catheter tip of a microcatheter is then directed to a vascular site by use of an aqueous solution containing an aqueous based contrast agent and the syringe is then mated to a microcatheter luer hub. The fluid composition is injected into the microcatheter and then into the vascular site under conditions which embolize the vascular site.

In another of its method aspects, this invention provides a method for inhibiting premature precipitation of a biocompatible polymer in a fluid composition designed to form a solid mass in vivo which composition is delivered by a microcatheter to a vascular site of a mammal where it precipitates and embolizes the vascular site. In this method, the composition is selected and placed into a syringe. The syringe comprises:

(a) a syringe body for holding a fluid composition,
(b) an ejection port,
(c) a means for ejecting the fluid composition in the syringe body through the ejection port and out of the syringe; and
(d) a means for mating said syringe body to a catheter luer hub.

A catheter tip of a microcatheter is then directed to a vascular site by use of an aqueous solution containing an aqueous based contrast agent and the syringe is then mated to a microcatheter luer hub comprising:

(a) a luer hub body for holding a fluid composition and a catheter delivery line attached to the luer hub body wherein the luer hub body has a maximal volumetric capacity such that the amount of solvent mixing is reduced when the fluid composition in injected therein in the presence of a residual aqueous solution, and
(b) at least one means for mating the luer hub body to a syringe. The fluid composition is injected into the microcatheter and then into the vascular site under conditions which embolize the vascular site.

Preferably, the luer hub body has a maximal volumetric capacity of no more than 0.2 cc.

Preferably, the novel luer hub defined herein is used in combination with the novel syringe also defined herein.

In a preferred embodiment, this invention provides for a syringe/catheter combination comprising:

(a) a catheter comprising a luer hub for holding a fluid composition and a delivery means attached to luer hub body, and at least one means for mating the luer hub body to a syringe,
(b) a syringe comprising a syringe body for holding a fluid composition, an ejection port, a means for ejecting the fluid composition out of the syringe, and a means for mating the syringe body to a catheter luer hub such that the dead space arising from mating said syringe body to said catheter is reduced.

The invention further provides a kit of parts comprising:

(1) a syringe which comprises: (a) a syringe body for holding a fluid composition, (b) an ejection port having an annular wall and an orifice which extends from the syringe body to a distal end of said port wherein said annular wall is tapered at the distal end along the length of at least a portion of the ejection port, (c) a means for ejecting the fluid composition in the syringe body through the ejection port and out of the syringe, and (d) a means for mating said syringe body to a catheter luer hub; and (2) a microcatheter luer hub which mates to the syringe.

In a preferred aspect, the kit of parts also includes a composition comprising (a) a biocompatible polymer; (b) a contrast agent; and (c) a biocompatible solvent.

In another preferred aspect, the microcatheter luer hub employed in this kit comprises (a) a luer hub body for holding a fluid composition and a catheter delivery line attached to luer hub body wherein the luer hub body has a maximal volumetric capacity such that the amount of solvent mixing is reduced when the fluid composition in injected therein in the presence of a residual aqueous solution, and, and (b) at least one means for mating the luer hub body to a syringe.

BRIEF DESCRIPTION OF THE DRAWINGS

The present invention can be further understood with reference to the following description in conjunction with the appended drawings, wherein like elements are provided with the same reference numerals. In the drawings.

DETAILED DESCRIPTION OF THE INVENTION

Figure 2A:
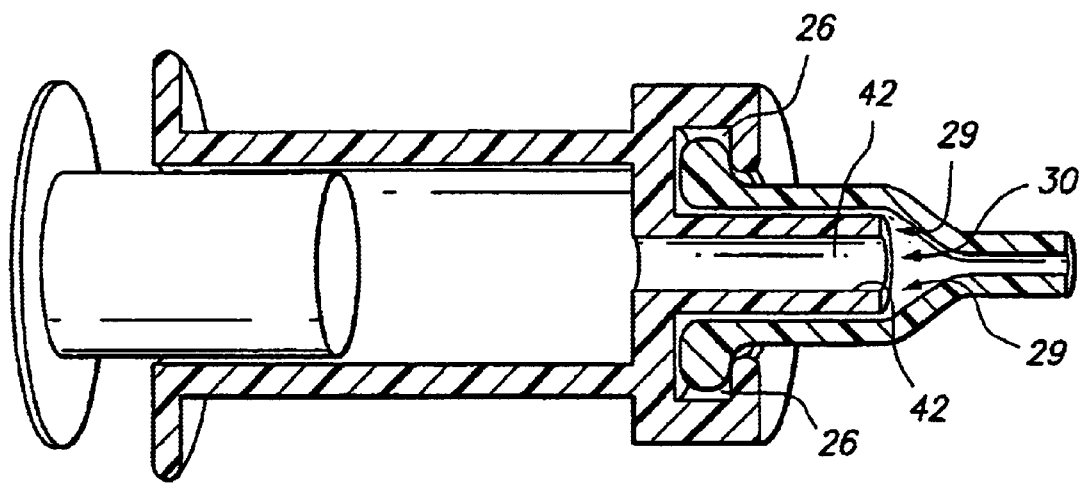
FIG. 2A shows a vertical cross-section view of a prior art ejection port mated with a microcatheter luer hub which form dead spaces when mated with a microcatheter luer hub.

The invention, which will be described in detail below, arose from the recognition that the cause of premature precipitation of fluid compositions comprising a biocompatible polymer is residual water (e.g., in the form of saline) or other precipitating agents that remain in the microcatheter luer hub after flushing of the microcatheter with a non-aqueous solvent. As shown in FIG. 2A, dead spaces 29 are created during flushing of the microcatheter because the prior art syringe employs an ejection port which is flat at the distal end mated with a luer hub having a tapered inner wall. As water (e.g., in the form of saline) passes out of the ejection port from the relatively small orifice diameter into the larger volume of the microcatheter luer hub immediately adjacent the flat distal end of the ejection port, it eddies in dead spaces 29. Accordingly, after introduction of a water solution into the catheter, flushing of the luer hub with the non-aqueous solvent may not remove all of the water particularly if the water is trapped in these dead spaces. Subsequently, residual water in the luer hub can mix with compositions containing a biocompatible polymer solubilized in a solvent but insoluble in water and cause precipitation of the biocompatible polymer.

Additionally, microcatheter luer hubs having a large volumetric capacity result in mixing of the non-aqueous solvent, e.g., ethanol and DMSO, introduced via syringe with water already present in the luer hub. Since the non-aqueous solvent is water miscible, an aqueous solution is created in the luer hub upon injection of the non-aqueous solvent. In such solutions, the amount of non-aqueous solvent required to completely flush out the water from the luer hub is proportional to the volumetric capacity of the luer hub; the larger the volumetric capacity, the more non-aqueous solvent is required. However, the intra-arterial infusion of DMSO or ethanol can produce local toxicity on the blood vessel and the use of large quantities of these solvents merely to flush water from the catheter is contra-indicated. See, for example, Sampei, et al., *Interventional Neuroradiology*, for "Histological Changes in Brain Tissue and Vasculature after Intracarotid Infusion of Organic Solvents in Rats", 38:291 (1996); Laurent, et al., *Abstract No. 299*, for "Injectable Gel-Giving Solutions for Embolization. Hydrodynamic and Animal Studies" Meeting of Interventional Radiology (1996); and Chaloupka, *Amer. Jour. Neur. Rad.*, 15:1107 (1994).

The presence of residual water in the luer hub can lead to premature precipitation of the biocompatible polymer which is particularly of concern with catheter delivery of a fluid composition comprising such a polymer because the catheter lines have such a small internal diameter that even modest amounts of precipitation can lead to clogging of these lines.

Prior to discussing the present invention in further detail, the following terms are defined:

The term "embolizing" or "embolization" refers to a process wherein a fluid composition comprising a biocompatible polymer in is injected into a blood vessel which, in the case of, for example, aneurysms, fills or plugs the aneurysm sac and/or encourages clot formation so that blood flow into the aneurysm ceases, and in the case of AVMs and AVFs forms a plug or clot to control/reroute blood flow to permit proper tissue perfusion. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic, chemically inert, and substantially non-immunogenic when used internally in the patient and which are substantially insoluble in blood and other aqueous solutions but are soluble in the fluid composition to the degree necessary to form a solid mass in vivo. Suitable biocompatible polymers include, by way of example, non-biodegradable polymers such as cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.[9] Other suitable biocompatible polymers include, for example, biodegradable polymers such as linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyhydroxybutyrates, polyhydroxyvalerates, polyalkylene oxalates, polyalkylene succinates, poly(malic acid), poly(amino acids), polyhydroxycellulose, chitin, chitosan, and copolymers, terpolymers and combinations thereof.

Preferably, the biocompatible polymer does not cause adverse inflammatory reactions when employed in vivo.

The particular biocompatible polymer employed is selected relative to the viscosity of the resulting polymer solution, the solubility of the biocompatible polymer in the biocompatible solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to about 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "contrast agent" refers to both water insoluble and aqueous based contrast agents.

"Water insoluble contrast agents" refer to a water insoluble (i.e., has a water solubility of less than 0.01 mg/ml at 20° C.) material capable of being monitored during injection into a mammalian subject by, for example, radiography, magnetic resonance imaging (MRI), and the like. Examples of water insoluble contrast agents include tantalum, tantalum oxide and barium sulfate, which are commercially available in the proper form for in vivo use. Preferably, the water insoluble contrast agent has an average particle size of about 10 μm or less. Methods for preparing such water insoluble biocompatible contrast agents having an average particle size of about 10 μm or less are described below. Other water insoluble contrast agents include, but are not limited to, gold, tungsten and platinum.

The term "aqueous based contrast agent" refers to a water soluble, biocompatible (non-toxic) radiopaque material capable of being monitored during injection into a mammalian subject by, for example, radiography. Examples of aqueous based contrast agents include metrizamide, iopamidol, iothalamate sodium, iodomide sodium, and meglumine.

The term "biocompatible solvent" refers to solvents capable of dissolving the selected biocompatible polymer, are miscible or soluble in aqueous compositions (e.g., blood). Suitable biocompatible solvents include ethanol, dimethylsulfoxide, acetone, and the like as well as aqueous mixtures thereof having no more than about 30 percent water. When employed at this level, the amount of water is sufficiently small that the dissolved polymer precipitates upon contact with the blood. Preferably, the biocompatible solvent is anhydrous and, even more preferably, the biocompatible solvent is anhydrous dimethylsulfoxide.

The term "encapsulation" as used relative to the water insoluble contrast agent being encapsulated in the polymer precipitate is not meant to infer any physical entrapment of the water insoluble contrast agent within the precipitate much as a capsule encapsulates a medicament. Rather, this term is used to mean that an integral coherent precipitate forms which does not separate into individual components.

The term "catheter" includes both catheters and microcatheters.

The term "taper" means a gradual diminution of the thickness of the annular wall to reduce dead space when mated with a luer hub.

The term "fluid" or "fluid composition" includes both fluid solutions, emulsions, and suspensions having a viscosity of less than about 300 centipoise at 20° C. and preferably about 100 centipoise or less at 20° C. Such fluid compositions are exemplified by compositions comprising a biocompatible solvent, a biocompatible polymer and a contrast agent. When the contrast agent is soluble in the biocompatible solvent, a fluid solution is obtained whereas when the contrast agent is insoluble in the biocompatible solvent, a fluid suspension is formed.

Figure 1A:
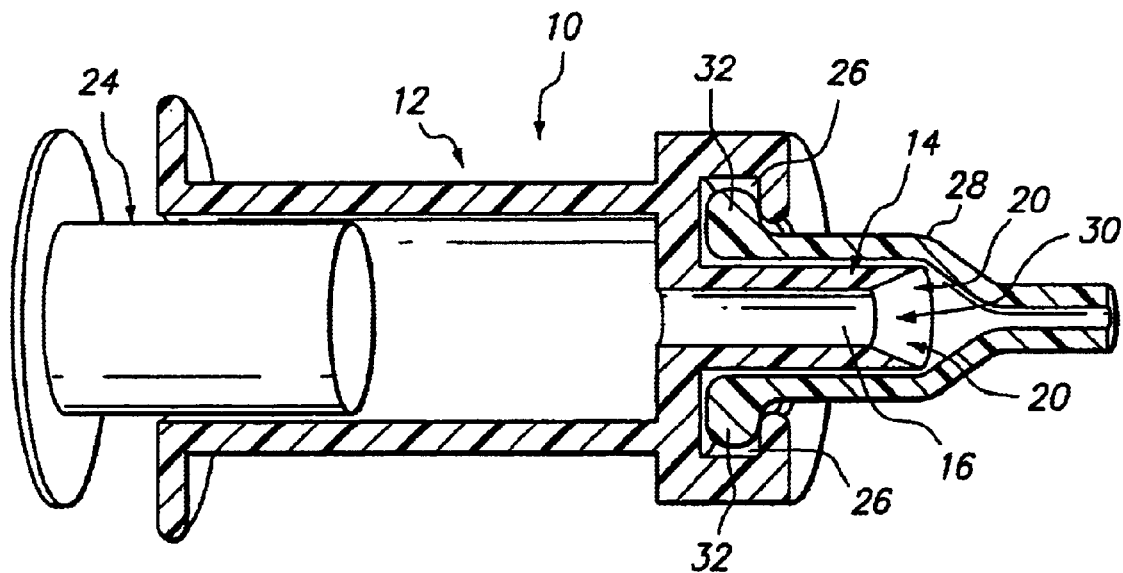
FIG. 1A shows a cross-section of the syringe of the present invention mated with a microcatheter luer hub.
Figure 1B:
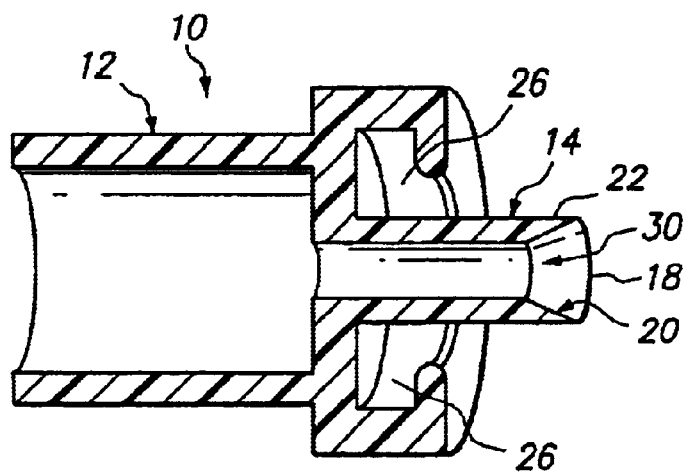
FIG. 1B shows a cross-section of the syringe of the invention without the luer hub.

FIGS. 1A and 1B show a syringe 10 having a syringe body 12 for holding fluid, an ejection port 14 having an orifice 16 extending from the syringe body 12 to the distal end of the ejection port 14 where, in the illustrated embodiment, orifice 16 is defined by inner 20 and outer walls 22 of the ejection port. The syringe also includes an ejection means 24 for injecting the fluid in the syringe body 12 through the ejection port 14 and out of the syringe. The syringe also has a mating means 26 to mate the syringe body 12 to a microcatheter luer hub 28. Mating means of FIG. 1A comprise a depression 26 wherein complementary protrusions 32 of the luer hub 28 (also depicted in FIG. 3) mate. Other suitable mating means well understood in the art can be employed including, by way of example, screw/thread combinations, twist-locks, luer slips, O-ring seals, bayonet fittings, needle interference fit and the like.

Other ejection means 24 in syringe 10 include, by way of example, syringe pumps, peristaltic pumps, and the like.

The inner wall 20 of orifice 16 of ejection port 14 is tapered from the distal end 18 of the ejection port along at least a portion of the length of ejection port 14. More particularly, the inner wall 20 is tapered so as to reduce the amount of dead or empty space present when the syringe is mated with a microcatheter luer hub.

In practice, the syringe may be formed such that the ejection port 14 and the syringe body 12 are formed as a single piece as shown in FIGS. 1A and 1B. Additionally, the syringe body may be formed such that the outer or inner wall of the syringe is threaded to receive an ejection port (not shown). The ejection port may be a needle which is mated to the threaded inner or outer wall of the syringe.

FIG. 1A depicts the combination of a syringe mated with a microcatheter luer hub and shows the interface between the syringe and the microcatheter luer hub. Specifically, in FIG. 1A, the luer hub/syringe interface is formed by mating the terminal ejection site 30 of the syringe via depression 26 with complementary protrusion 32 of luer hub 28 which secures the syringe to the microcatheter. The inner walls 20 of the ejection port of the syringe are tapered to decrease the "dead space" in the mixing area and to prevent settling of insoluble material behind these walls.

Figure 2B:
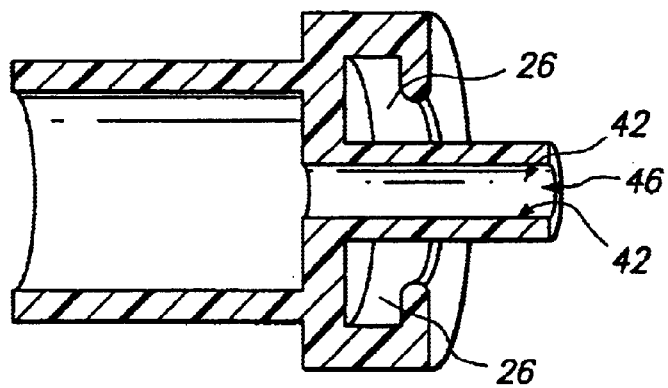
FIG. 2B shows a vertical cross-section of the prior art ejection port for a syringe without the luer hub.

FIGS. 2A and 2B show that this tapering feature is particularly important since non-tapered inner wall 42 of a conventional injection port 46 will allow the formation of dead space 29 behind this wall as the fluid compositions flow past. Such dead spaces invariably result in vortexes or eddies forming which concomitantly results in retention of materials flowing there past, such as the aqueous solution of the aqueous based contrast agent. Upon injection of a fluid composition comprising a biocompatible polymer and a biocompatible solvent, contact of this composition with the aqueous solution results in the precipitation of the biocompatible polymer which can result in plugging or clogging of the microcatheter orifice or the catheter delivery lines.

Figure 4:
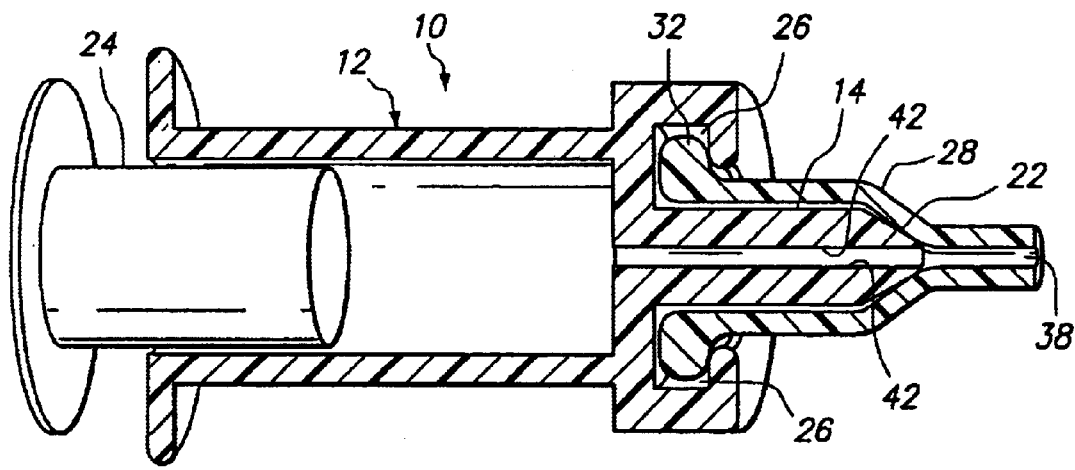
FIG. 4 shows a vertical cross-section of an ejection port of this invention having alternative tapering of the annular wall.

In the embodiment illustrated in FIG. 1B, tapering of the inner wall of the ejection port decreases the amount of dead space in the interface between the ejection port and the luer head. However, various degrees of tapering which decreases this dead space may be employed. For instance, a decrease of the thickness of the wall of the ejection port at the distal end will decrease the dead space in the interface with the luer head as shown in FIG. 4. Specifically, FIG. 4 illustrates that tapering of outer wall 22 to match the contour of the inner wall of microcatheter luer hub 28 will also reduce dead space.

Figure 5:
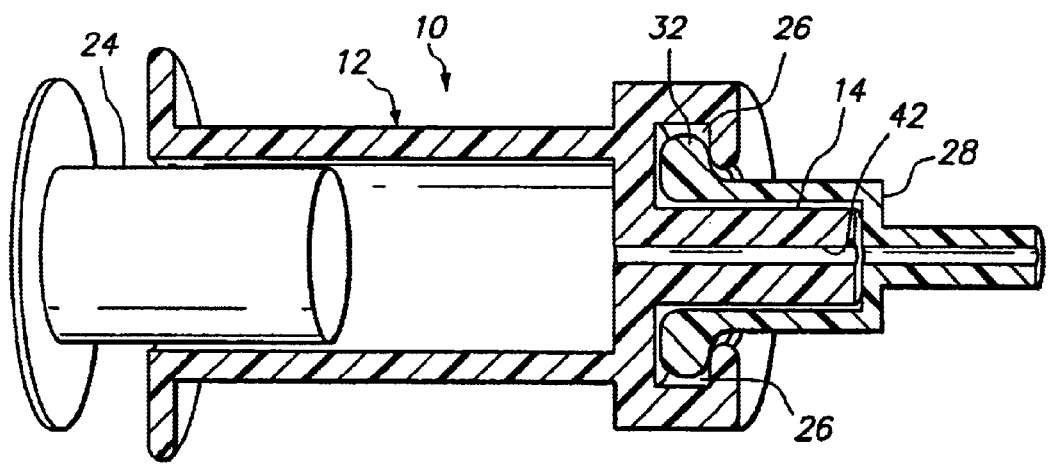
FIG. 5 shows still a further illustration of an ejection port/luer hub design which reduces dead space associated therewith.

Still further, any means for reducing dead space in the luer hub/syringe combination can be used. For example, FIG. 5 illustrates that size matching of the orifice of injection port 46 via non-tapered walls 42 with orifice 38 of catheter 34 also reduces dead space.

Figure 3:
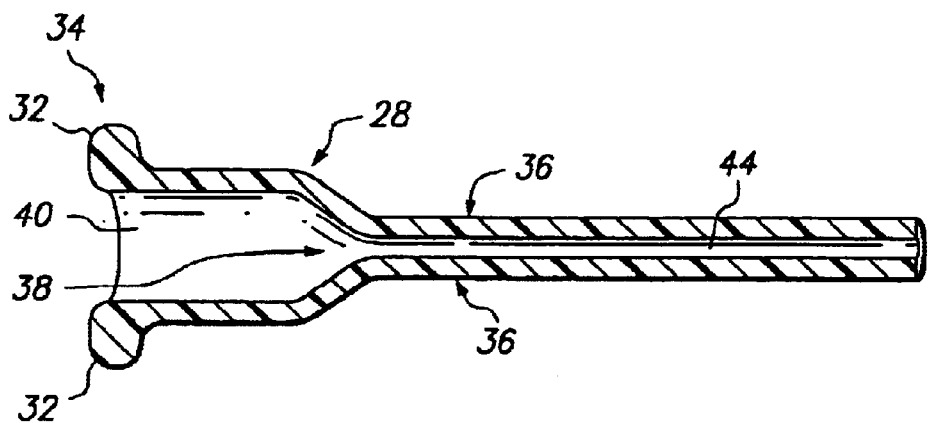
FIG. 3 shows a vertical cross-section of a luer hub.

FIG. 3 shows the catheter luer hub of FIG. 1A without the attached syringe. In this embodiment, the protrusions 32 of luer hub 28 mate with complementary depression 26 of syringe 10 (not shown) to secure the syringe to the catheter 34. Walls 36 of the luer hub 28 taper quickly to orifice 38 which defines the internal passage in the delivery means 44 of catheter 34. Rapid tapering reduces volumetric space 40 of the luer hub 28 and further results in a tight fit with the syringe when so fitted. Preferably, volumetric space 40 of the luer hub is less than about 0.2 cc and more preferably less than about 0.1 cc. When so limited, mixing of different solutions in the dead space of the luer hub is minimized and this, in turn, reduces premature precipitation of the fluid composition.

The delivery means 44 in catheter 34 include flexible tube defining an orifice which extends from the luer hub to the distal end of the tube thereby permitting transport of, e.g., the fluid composition, from the luer hub to the distal end located at the vascular site to be embolized. The orifice in the flexible tube of the catheter 34 is preferably large enough to permit ejection of the fluid composition from syringe 10 to the vascular site without undue pressure while being small enough to permit placement of the catheter tube intravascularly. Preferably, the orifice has a diameter of from about 0.25 to about 2 mm.

In the catheter delivery methods described herein, a small diameter medical catheter (i.e., microcatheter) having a diameter typically from about 1 mm to about 3 mm is preferably employed. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., polytetrafluoroethylene, perfluoroalkoxy resin, fluorinated ethylene propylene polymers, etc.), silicone, etc. The specific polymer employed is selected relative to stability in the presence of DMSO.

In one preferred embodiment, the specific catheter delivery technique for delivering a composition forming a solid mass in vivo encompasses the following:

1. Shake a fluid composition comprising a biocompatible polymer, a biocompatible solvent and a biocompatible water insoluble contrast agent for about 4 minutes until the contrast agent is fully dispersed;
2. Place the delivery means of the microcatheter at the site of intended vascular embolization while confirming microcatheter placement in vivo by injection of aqueous based contrast agent;
3. Connect a syringe containing saline to the luer hub of the microcatheter and flush the aqueous based contrast agent from the microcatheter hub and body with about 5 cc of saline over an approximately 1 minute period with gentle pulsing at 1 cc increments. Repeat with another 5 cc of saline if the volume can be tolerated. Leave the syringe connected or secure a cap on the microcatheter luer hub;
4. Aspirate approximately 0.8 cc of sterile DMSO into a 1 cc syringe. Remove cap from microcatheter hub. Inject 0.30 cc of DMSO for a typical 150 cm microcatheter. While the DMSO is being prepared and injected, shake the fluid composition for about 2 minutes to fully disperse the water insoluble contrast agent. Fill a 1 cc syringe with the fluid composition. As soon as the DMSO has been injected, remove the syringe and overfill/wash with the balance of the DMSO;
5. Immediately connect the syringe containing the fluid composition to the catheter hub, making sure that there is no air in the hub during the connection;
6. With the composition syringe pointing up to create a sharp interfacial boundary between the DMSO and the fluid composition which boundary is facilitated by the use of the syringe/luer hub combination of this invention, slowly inject the first 0.25 cc (150 cm catheter) over a 1 minute period to displace the DMSO in the microcatheter and dilute the DMSO in the blood;
7. Under fluoroscopy, the fluid composition may be visible in the distal portion of the microcatheter body. Lower the syringe tip and inject the fluid composition as the clinical situation requires. Monitor the volume of the fluid composition injected to correspond to the volume of the vascular space being filled; and
8. Upon completion of the fluid composition injection, gently aspirate with the embolic syringe to separate the catheter tip from the solid composition mass formed in vivo. Wait a few seconds, release the syringe plunger and withdraw the microcatheter.

In this protocol, the dead space for the 150 cm microcatheter is about 0.32 cc.

In the case of aneurysms, the mammal is preferably rotated to place the aneurysm in a downward position to encourage displacement of aneurysmal blood upon injection.

When introduced into the vascular site, the biocompatible solvent diffuses rapidly into the blood and a solid precipitate forms which precipitate is the bicompatible polymer with the water insoluble contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

The following examples are offered for illustrative purposes only and are not to be construed in any way as limiting the scope of the present invention. Unless otherwise stated, all temperatures are in degrees Celsius.

EXAMPLE 1

Fluid compositions useful with the syringe and catheters described herein include compositions comprising (a) a biocompatible polymer; (b) a contrast agent; and (c) a biocompatible solvent.

This example demonstrates the preparation of one such fluid composition.

Specifically, an EVOH polymer composition was prepared as follows:

Composition

A) 8 gm EVOH (biocompatible polymer);

B) 30 gm tantalum (contrast agent) having an average particle size of less than about 10 $\mu$m (narrow size distribution); and C) 100 mL DMSO (biocompatible solvent).

Each of the components of this composition were combined and the resulting mixture was mixed until homogeneous. In this composition, the average particle size of the contrast agent was prepared by fractionation wherein tantalum, having an average particle size of less than about 20 $\mu$m, was added to ethanol (absolute) in a clean environment. Agitation of the resulting suspension was followed by settling for approximately 40 sec. to permit the larger particles to settle faster. Removal of the upper portion of the ethanol followed by separation of the fluid from the particles results in a reduction of the particle size which is confirmed under a microscope (Nikon Alphaphot™). The process was repeated, as necessary, until an average 3 $\mu$m particle size was reached.

Other preferred compositions include, by way of example, those comprising:

(a) from about 2.5 to about 8.0 weight percent of a biocompatible polymer;

(b) from about 10 to about 40 weight percent of a water soluble or insoluble contrast agent; and (c) from about 52 to about 87.5 weight percent of a biocompatible solvent wherein the weight percent of the biocompatible polymer, contrast agent and biocompatible solvent is based on the total weight of the complete composition.

EXAMPLE 2

This example illustrates a specific protocol for embolizing mammalian blood vessels by delivering a fluid composition of Example 1 to a vascular site using a catheter/syringe combination of this invention.

In this example, a 20 kg red Duroc swine with rete mirabile located in the lower portions (left and right) of the skull base was anesthetized. The fluid composition of Example 1 above was shaken for about 4 minutes until the contrast agent was fully dispersed. A 150 cm microcatheter with a luer hub having 0.1 cc volumetric capacity was placed through a femoral artery access at the site of intended vascular embolization, the rete mirabile (a well accepted AVM model), using a 0.014 inch guidewire while confirming microcatheter placement by injection of aqueous based contrast agent (e.g., Omnipaque™ available from Nycomed, Princeton, N.J.). After placement, a syringe containing saline was connected to the luer hub of the microcatheter and the aqueous based contrast agent was flushed from the microcatheter hub and body with about 5 cc of saline over an approximately 1 minute period with gentle pulsing at 1 cc increments. An additional 5 cc of saline can optionally be used and the process repeated.

Afterwards, the syringe was removed and a cap was secured on the microcatheter luer hub. Sterile DMSO (not less than 0.5 cc and preferably 0.8 mL)) was aspirated into a 1 cc syringe of FIG. 1A having a tapered ejection port. The cap was removed from the microcatheter hub and the syringe fitted thereto. About 0.30 cc of DMSO was injected into the catheter to remove the saline therefrom.

While the DMSO was being prepared and injected, the fluid composition was shaken for about 2 minutes to fully disperse the water insoluble contrast agent. A 1 cc syringe of FIG. 1A having a tapered ejection port was then filled with the fluid composition using a 21 gage needle. As soon as the DMSO was injected, the syringe was removed and the balance of the DMSO used for overfilling and washing the luer hub.

Afterwards, the syringe containing the fluid composition was immediately connected to the catheter hub, making sure that there was no air in the hub during the connection. With the composition syringe pointing up to create a sharp interfacial boundary between the DMSO and the fluid composition, the first 0.25 cc was injected over approximately a 1 minute period to displace the DMSO in the microcatheter and dilute the DMSO in the blood. Under fluoroscopy, the fluid composition was visible in the distal portion of the microcatheter body. The syringe tip was lowered and the fluid composition then injected as the clinical situation requires. The volume of the fluid composition was monitored to ensure that the amount of fluid composition injected corresponded to the volume of the vascular space being filled (about 0.2 cc). Upon completion of the fluid composition injection, the syringe was gently aspirated to separate the catheter tip from the solid composition mass formed in vivo. After a few seconds, the syringe plunger was released and the microcatheter withdrawn.

From the foregoing description, various modifications and changes in the composition and method will occur to those skilled in the art. All such modifications coming within the scope of the appended claims are intended to be included therein.

What is claimed is:

1. A syringe/catheter combination comprising:

(a) a catheter comprising a luer hub having a luer hub body for holding a fluid composition, a delivery means attached to the luer hub body, and at least one means for mating the luer hub body to a syringe, and (b) a syringe comprising a syringe body for holding a fluid composition, an ejection port terminating in said luer hub body, a means for ejecting the fluid composition out of the syringe through said ejection port into said luer hub body, and a means for mating the syringe body to a catheter luer hub such that the dead space arising from mating said syringe body to said catheter is reduced, said means for mating including a taper of a distal end of a wall of the ejection port.

2. A kit of parts comprising:

(1) a syringe which comprises: (a) a syringe body for holding a fluid material, (b) an ejection port having an annular wall and an orifice which extends from the syringe body to a distal end of said port wherein said annular wall is tapered at the distal end along the length of at least a portion of the ejection port, (c) means, including a luer hub body, for mating said syringe body to a microcatheter, (d) and a means for ejecting a composition in the syringe body through the ejection port into the luer hub body and out of the syringe; and (2) a microcatheter which mates to the syringe.

3. The kit of parts according to claim 2 which further comprises a composition comprising (a) a biocompatible polymer; (b) a contrast agent; and (c) a biocompatible solvent.

4. A kit of parts comprising:

(1) a syringe which comprises: (a) a syringe body for holding a fluid material, (b) an ejection port, (c) a means for ejecting a composition in the syringe body through the ejection port and out of the syringe, and (d) a means for mating said syringe body to a microcatheter; and (2) a microcatheter comprising (a) a luer hub body for holding a fluid material and a catheter delivery line attached to luer hub body wherein the luer hub body has a maximal volumetric capacity of no more than 0.2 cc, and (b) at least one means for mating the luer hub body to a syringe.

5. The kit of parts according to claim 4 which further comprises a composition comprising (a) a biocompatible polymer; (b) a contrast agent; and (c) a biocompatible solvent.

6. The kit of parts of claim 2, wherein said annular wall is an inner wall, said taper resulting in an increase in a diameter of said orifice such that said orifice expands away from the syringe body.

7. The kit of parts of claim 2, wherein said annular wall is an outer wall, said taper resulting in a contour which matches an interior contour of the luer hub body.

* * * * *